United States Patent
Eby

(10) Patent No.: US 7,291,769 B2
(45) Date of Patent: Nov. 6, 2007

(54) SOYBEAN CULTIVAR 4348019

(75) Inventor: William H. Eby, Panora, IA (US)

(73) Assignees: Stine Seed Farm, Inc., Adel, IA (US); Monsanto Technology LLC, St. Louis, MO (US)

( * ) Notice: Subject to any disclaimer, the term of this patent is extended or adjusted under 35 U.S.C. 154(b) by 332 days.

(21) Appl. No.: 11/065,321

(22) Filed: Feb. 24, 2005

(65) Prior Publication Data

US 2006/0191031 A1    Aug. 24, 2006

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. ............ 800/312; 800/260; 800/263; 800/264; 800/265; 800/279; 800/281; 800/284; 800/286; 800/300; 800/301; 800/302; 435/415; 435/426; 435/430

(58) Field of Classification Search ........... 800/312
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 6/1996 | Hunsperger et al. |
| 5,850,009 | A | 12/1998 | Kevern |
| 5,917,132 | A | 6/1999 | Eby |
| 5,968,830 | A | 10/1999 | Dan et al. |
| 7,022,901 | B1 * | 4/2006 | Schultze ............ 800/312 |

OTHER PUBLICATIONS

Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. App. Genet. 101:323-326.
Willmot, et al., 1989. Genetic analysis of brown stem rot resistance in soybean. Crop Sci. 29:672-674.
Narvel, et al., 2001. A Retrospective DNA Marker Assessment of the Development of Insect Resistant Soybean Crop Sci. 41:1931-1939.
Poehlman, J.M. and Sleper, D.A., Methods in Plant Breeding, *In* Breeding Field Crops, 4th ed. (1995), Iowa State University Press, pp. 172-174.
Goldman, et al., 1994. Molecular Markers Associated with Maize Kernel Oil Concentration in an Illinois High Protein x Illinois Low Protein Cross. Crop Sci. 34: 908-915.

* cited by examiner

*Primary Examiner*—Cynthia Collins
(74) *Attorney, Agent, or Firm*—Jondle & Associates, P.C.

(57) ABSTRACT

A soybean cultivar designated 4348019 is disclosed. The invention relates to the seeds of soybean cultivar 4348019, to the plants of soybean 4348019, to plant parts of soybean cultivar 4348019 and to methods for producing a soybean plant produced by crossing soybean cultivar 4348019 with itself or with another soybean variety. The invention also relates to methods for producing a soybean plant containing in its genetic material one or more transgenes and to the transgenic soybean plants and plant parts produced by those methods. This invention also relates to soybean cultivars or breeding cultivars and plant parts derived from soybean variety 4348019, to methods for producing other soybean cultivars, lines or plant parts derived from soybean cultivar 4348019 and to the soybean plants, varieties, and their parts derived from use of those methods. The invention further relates to hybrid-soybean seeds, plants and plant parts produced by crossing the cultivar 4348019 with another soybean cultivar.

22 Claims, No Drawings

SOYBEAN CULTIVAR 4348019

BACKGROUND OF THE INVENTION

The present invention relates to a new and distinctive soybean cultivar, designated 4348019. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of soybean plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions and further selections are then made during and at the end of the growing season. The cultivars that are developed are unpredictable because the breeder's selection occurs in unique environments with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max* L. Merr.) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD and three classical markers and four isozyme loci. See also, Shoemaker, R. C., RFLP Map of Soybean, p 299-309, in Phillips, R. L. and Vasil, I. K. (eds.) DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation breeding is another method of introducing new traits into soybean varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of soybean plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have traits that result in superior cultivars.

SUMMARY OF THE INVENTION

According to the invention, there is provided a novel soybean cultivar designated 4348019. This invention thus relates to the seeds of soybean cultivar 4348019, to the plants of soybean 4348019 and to methods for producing a soybean plant produced by crossing the soybean 4348019 with itself or another soybean line, and the creation of variants by mutagenesis or transformation of soybean 4348019.

Thus, any such methods using the soybean cultivar 4348019 are part of this invention: selfing, backcrosses, hybrid production, crosses to populations, and the like. All plants produced using soybean cultivar 4348019 as a parent are within the scope of this invention. Advantageously, the soybean cultivar could be used in crosses with other, different, soybean plants to produce first generation ($F_1$) soybean hybrid seeds and plants with superior characteristics.

In another aspect, the present invention provides for single or multiple gene converted plants of 4348019. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, and industrial usage. The gene may be a naturally occurring soybean gene or a transgene introduced through genetic engineering techniques.

In another aspect, the present invention provides regenerable cells for use in tissue culture of soybean plant 4348019. The tissue culture will preferably be capable of regenerating plants having the physiological and morphological characteristics of the foregoing soybean plant, and of regenerating plants having substantially the same genotype as the foregoing soybean plant. Preferably, the regenerable cells in such tissue cultures will be embryos, protoplasts, meristematic cells, callus, pollen, leaves, anthers, roots, root tips, flowers, seeds, pods or stems. Still further, the present invention provides soybean plants regenerated from the tissue cultures of the invention.

DEFINITIONS

In the description and tables that follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Brown Stem Rot. This is a visual disease score from 1 to 9 comparing all genotypes in a given test. The score is based on leaf symptoms of yellowing and necrosis caused by brown stem rot. Visual scores range from a score of 9, which indicates no symptoms, to a score of 1 which indicates severe symptoms of leaf yellowing and necrosis.

Cotyledon. A cotyledon is a type of seed leaf. The cotyledon contains the food storage tissues of the seed.

Embryo. The embryo is the small plant contained within a mature seed.

Emergence. This score indicates the ability of the seed to emerge when planted 3" deep in sand at a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

Hilum. This refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron-Deficiency Chlorosis. Plants are scored 1 to 9 based on visual observations. A score of 9 means no stunting of the plants or yellowing of the leaves and a score of 1 indicates the plants are dead or dying caused by iron-deficiency chlorosis, a score of 5 means plants have intermediate health with some leaf yellowing.

Lodging Resistance. Lodging is rated on a scale of 1 to 9. A score of 9 indicates erect plants. A score of 5 indicates plants are leaning at a 45° angle in relation to the ground and a score of 1 indicates plants are lying on the ground.

Maturity Date. Plants are considered mature when 95% of the pods have reached their mature color. The number of days are calculated either from August 31 or from the planting date.

Maturity Group. This refers to an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

Relative Maturity (RM). The term relative maturity is a numerical value that is assigned to a soybean variety based on comparisons with the maturity values of other varieties. The number preceding the decimal point in the RM refers to the maturity group. The number following the decimal point refers to the relative earliness or lateness within each maturity group. For example, a 3.0 is an early group III variety, while a 3.9 is a late group III variety.

Oil or oil percent. Soybean seeds contain a considerable amount of oil. Oil is measured by NIR spectrophotometry, and is reported on an as is percentage basis.

Oleic Acid Percent. Oleic acid is one of the five most abundant fatty acids in soybean seeds. It is measured by gas chromatography and is reported as a percent of the total oil content.

Palmitic Acid Percent. Palmitic acid is one of the five most abundant fatty acids in soybean seeds. It is measured by gas chromatography and is reported as a percent of the total oil content.

*Phytophthora* Tolerance. Tolerance to *Phytophthora* root rot is rated on a scale of 1 to 9, with a score of 9 being the best or highest tolerance ranging down to a score of 1 which indicates the plants have no tolerance to *Phytophthora*.

Phenotypic Score. The Phenotypic Score is a visual rating of general appearance of the variety. All visual traits are considered in the score including healthiness, standability, appearance and freedom of disease. Ratings are scored from 1 being poor to 9 being excellent.

Plant Height. Plant height is taken from the top of soil to the top node of the plant and is measured in centimeters.

Pod. This refers to the fruit of a soybean plant. It consists of the hull or shell (pericarp) and the soybean seeds.

Protein Percent. Soybean seeds contain a considerable amount of protein. Protein is generally measured by NIR spectrophotometry, and is reported on an as is percentage basis.

Pubescence. This refers to a covering of very fine hairs closely arranged on the leaves, stems and pods of the soybean plant.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity is defined as a chemical taxonomic technique to separate cultivars based on the presence or absence of the peroxidase enzyme in the seed coat. There are two types of soybean cultivars, those having high peroxidase activity (dark red color) and those having low peroxidase activity (no color).

Seed Yield (Bushels/Acre). The yield in bushels/acre is the actual yield of the grain at harvest.

Seeds per Pound. Soybean seeds vary in seed size, therefore, the number of seeds required to make up one pound also varies. This affects the pounds of seed required to plant a given area, and can also impact end uses.

Shattering. The amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION 4348019 is a mid maturity group I variety with resistance to ROUNDUP herbicide conferring tolerance to glyphosate herbicides. 4348019 also has the Rps 1k gene which confers resistance to *Phytophthora* root rot. 4348019 has very high yield potential when compared to lines of similar maturity and has excellent agronomic characteristics including lodging resistance.

Some of the selection criteria used for various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The line has been increased with continued observation for uniformity.

Soybean cultivar 4348019 has the following morphologic and other characteristics (based primarily on data collected at Adel, Iowa).

TABLE 1

VARIETY DESCRIPTION INFORMATION

Seed Coat Color (Mature Seed): Yellow
Seed Coat Luster (Mature Hand Shelled Seed): Dull
Cotyledon Color (Mature Seed): Yellow
Leaflet Shape: Ovate
Growth Habit: Indeterminate
Flower Color: Purple
Hilum Color (Mature Seed): Black
Plant Pubescence Color: Light tawny
Pod Color: Tan
Maturity Group: I
Relative Maturity: 1.4
Plant Lodging Score: 8
Plant Height (cm): 66
Seed Size (# Seeds/lb.): 2890
Seed Content:

% Protein: 36.8
% Oil: 18.2

Physiological Responses: ROUNDUP READY Herbicide Resistant

Disease Resistance: *Phytophthora* root rot—Rps 1k

This invention is also directed to methods for producing a soybean plant by crossing a first parent soybean plant with a second parent soybean plant, wherein the first or second soybean plant is the soybean plant from the line 4348019. Further, both first and second parent soybean plants may be from the cultivar 4348019. Therefore, any methods using the cultivar 4348019 are part of this invention: selfing, backcrosses, hybrid breeding, and crosses to populations. Any plants produced using cultivar 4348019 as a parent are within the scope of this invention.

Useful methods include but are not limited to expression vectors introduced into plant tissues using a direct gene transfer method such as microprojectile-mediated delivery, DNA injection, electroporation and the like. More preferably, expression vectors are introduced into plant tissues using the microprojectile media delivery with the biolistic device or *Agrobacterium*-mediated transformation. Transformant plants obtained with the protoplasm of the invention are intended to be within the scope of this invention.

Soybean cultivar 4348019 is similar to 400644-23. While similar to 400644-23 there are numerous differences including: 4348019 has the gene for resistance to the ROUNDUP herbicides and 400644-23 does not contain this gene. Additionally, 4348019 has black hila while 400644-23 has brown hila.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed soybean plants, using transformation methods as described below to incorporate transgenes into the genetic material of the soybean plant(s).

Expression Vectors for Soybean Transformation: Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990) Hille et al., Plant Mol. Biol. 7:171 (1986). Other selectable marker genes confer resistance to herbicides such as glyphosate, glufosinate or broxynil. Cornai et al., Nature 317:741-744 (1985), Gordon-Kamm et al., Plant Cell 2:603-618 (1990) and Stalker et al., Science 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984).

In vivo methods for visualizing GUS activity that do not require destruction of plant tissue are available. Molecular Probes publication 2908, IMAGENE GREEN, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters—Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. USA 88:0421 (1991).

Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); PEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, XbaI/NcoI fragment 5' to the *Brassica napus* ALS3 structural gene (or a nucleotide sequence similarity to said Xba1/NcoI fragment), represents a particularly useful constitutive promoter. See PCT application WO96/30530.

Tissue-specific or Tissue-preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments—Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes—With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is a soybean plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene(s) to engineer plants that are resistant to specific pathogen strains. See, for example Jones et al., Science 266:789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al. Cell 78:1089 (1994) (*Arabidopsis* RSP2 gene for resistance to *Pseudomonas syringae*).

B. A gene conferring resistance to a pest, such as soybean cyst nematode. See e.g., PCT Application WO96/30517; PCT Application WO93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., Plant Molec. Biol. 24:25 (1994), who disclose the nucleotide sequences of several *Clivia miniata* mannose-binding lectin genes.

E. A vitamin-binding protein such as avidin. See PCT application US93/06487 which teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO95/16776, which discloses peptide derivatives of Tachyplesin which inhibit fungal plant pathogens, and PCT application WO95/18855 which teaches synthetic antimicrobial peptides that confer disease resistance.

N. A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

T. Genes involved in the Systemic Acquired Resistance (SAR) Response and/or the pathogenesis related genes. Briggs, S. Current Biology, 5(2) (1995).

U. Antifungal genes. See Cornelissen and Melchers, Plant Physiol., 101:709-712 (1993); Parijs et al., Planta 183:258-264 (1991) and Bushnell et al., Can. J. of Plant Path. 20(2):137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (AC-Case inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Cornai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., Theor. Appl. Genet. 83:435 (1992).

C. An herbicide that inhibits photosynthesis, such as a triazine (psbA and gs+genes) and a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, such as:

A. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, for example, this could be accomplished by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley α-amylase gene), and Fisher et al., Plant Physiol. 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility:

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

Introduction of the barnase and the barstar genes. See Paul et al., Plant Mol. Biol. 19:611-622, 1992).

Methods for Soybean Transformation—Numerous methods for plant transformation have been developed including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation collectively referred to as direct gene transfer have been developed as an alternative to *Agrobacterium*-mediated transformation. A generally applicable method of plant surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987); Sanford, J. C., Trends Biotech. 6:299 (1988); Klein et al., Bio/Tech. 6:559-563 (1988); Sanford, J. C. Physiol Plant 7:206 (1990); Klein et al., Biotechnology 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985); Christou et al., Proc Natl. Acad. Sci. USA 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of soybean target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Single-Gene Conversions—When the term soybean plant is used in the context of the present invention, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term backcrossing as used herein refers to the repeated crossing of a hybrid progeny back to the recurrent parent, i.e., backcrossing 1, 2, 3, 4, 5, 6, 7, 8 or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic; examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference.

Further reproduction of the variety can occur by tissue culture and regeneration. Tissue culture of various tissues of soybeans and regeneration of plants therefrom is well known and widely published. For example, reference may be had to Komatsuda, T. et al., Crop Sci. 31:333-337 (1991); Stephens, P. A., et al., Theor. Appl. Genet. (1991) 82:633-635; Komatsuda, T. et al., Plant Cell, Tissue and Organ Culture, 28:103-113 (1992); Dhir, S. et al., Plant Cell Reports (1992) 11:285-289; Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce soybean plants having the physiological and morphological characteristics of soybean variety 4348019.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

This invention also is directed to methods for producing a soybean plant by crossing a first parent soybean plant with a second parent soybean plant wherein the first or second parent soybean plant is a soybean plant of the variety 4348019. Further, both first and second parent soybean plants can come from the soybean variety 4348019. Thus, any such methods using the soybean variety 4348019 are part of this invention: selfing, backcrosses, hybrid production, crosses to populations, and the like. All plants produced using soybean variety 4348019 as a parent are within the scope of this invention, including those developed from varieties derived from soybean variety 4348019. Advantageously, the soybean variety could be used in crosses with other, different, soybean plants to produce the first generation ($F_1$) soybean hybrid seeds and plants with superior characteristics. The variety of the invention can also be used for transformation where exogenous genes are introduced and expressed by the variety of the invention. Genetic variants created either through traditional breeding methods using variety 4348019 or through transformation of 4348019 by any of a number of protocols known to those of skill in the art are intended to be within the scope of this invention.

The following describes breeding methods that may be used with cultivar 4348019 in the development of further soybean plants. One such embodiment is a method for developing a 4348019 progeny soybean plant in a soybean plant breeding program comprising: obtaining the soybean plant, or a part thereof, of cultivar 4348019 utilizing said plant or plant part as a source of breeding material and selecting a 4348019 progeny plant with molecular markers in common with 4348019 and/or with morphological and/or physiological characteristics selected from the characteristics listed in Tables 1 or 2. Breeding steps that may be used in the soybean plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar 4348019 progeny soybean plants, comprising crossing cultivar 4348019 with another soybean plant, thereby producing a population of soybean plants, which, on average, derive 50% of their alleles from cultivar 4348019. A plant of this population may be selected and repeatedly selfed or sibbed with a soybean cultivar resulting from these successive filial generations. One embodiment of this invention is the soybean cultivar produced by this method and that has obtained at least 50% of its alleles from cultivar 4348019.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes soybean cultivar 4348019 progeny soybean plants comprising a combination of at least two 4348019 traits selected from the group consisting of those listed in Tables 1 and 2 or the 4348019 combination of traits listed in the Summary of the Invention, so that said progeny soybean plant is not significantly different for said traits than soybean cultivar 4348019 as determined at the 5% significance level when grown in the same environmental conditions. Using techniques described herein, molecular markers may be used to identify said progeny plant as an 4348019 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar 4348019 may also be characterized through their filial relationship with soybean cultivar 4348019, as for example, being within a certain number of breeding crosses of soybean cultivar 4348019. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean cultivar 4348019 and its progeny. For example, progeny produced by the methods described herein may be within 1, 2, 3, 4 or 5 breeding crosses of soybean cultivar 4348019.

As used herein, the term plant includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, and the like.

INDUSTRIAL USES

The seed of soybean variety 4348019, the plant produced from the seed, the hybrid soybean plant produced from the crossing of the variety with any other soybean plant, hybrid seed, and various parts of the hybrid soybean plant can be utilized for human food, livestock feed, and as a raw material in industry.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board and American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, lubricants and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

TABLES

In Table 2 that follows, the traits and characteristics of soybean cultivar 4348019 are compared to several competing varieties of commercial soybeans of similar maturity. In the tables, column 1 shows the comparison number; column 2 is the year of the test; columns 3 and 4 give the number of locations and number of observations, respectively. Column 5 indicates the genotype and column 6 shows the mean yield. Column 7 presents the t value and columns 8 and 9 present the critical t values at the 0.05% and 0.01% levels of significance, respectively.

As shown in Table 2 below, soybean cultivar 4348019 yields higher than 18 commercial varieties with the increase over all comparisons being significant at the 0.01 level of probability except CSR0944 and AG1401 where the increase is significant at the 0.05 level.

TABLE 2

PAIRED COMPARISONS

| Comp # | Year | # of Loc. | # of Obs. | Genotype | Mean Yield | t Value | Critical t @ .05 | Critical t @ .01 |
|---|---|---|---|---|---|---|---|---|
| 1 | 2004 | 16 | 45 | 4348019 | 46.0 | 4.15** | 1.68 | 2.41 |
|  |  |  |  | CSR1204 | 42.7 |  |  |  |
| 2 | 2004 | 16 | 47 | 4348019 | 46.1 | 2.28* | 1.68 | 2.41 |
|  |  |  |  | CSR0944 | 44.3 |  |  |  |
| 3 | 2004 | 16 | 47 | 4348019 | 46.1 | 4.43** | 1.68 | 2.41 |
|  |  |  |  | AG1001 | 42.1 |  |  |  |
| 4 | 2004 | 16 | 46 | 4348019 | 46.2 | 5.19** | 1.68 | 2.41 |
|  |  |  |  | CSR1003 | 40.9 |  |  |  |
| 5 | 2004 | 16 | 47 | 4348019 | 46.1 | 7.25** | 1.68 | 2.41 |
|  |  |  |  | NKS10-T1 | 39.6 |  |  |  |
| 6 | 2004 | 16 | 47 | 4348019 | 46.1 | 3.49** | 1.68 | 2.41 |
|  |  |  |  | AG1102 | 43.2 |  |  |  |
| 7 | 2004 | 16 | 47 | 4348019 | 46.1 | 7.40** | 1.68 | 2.41 |
|  |  |  |  | SG1330N | 39.9 |  |  |  |
| 8 | 2004 | 16 | 45 | 4348019 | 46.0 | 2.14* | 1.68 | 2.41 |
|  |  |  |  | AG1401 | 43.7 |  |  |  |
| 9 | 2004 | 16 | 44 | 4348019 | 45.7 | 3.64** | 1.68 | 2.41 |
|  |  |  |  | BPR2288 | 40.9 |  |  |  |
| 10 | 2004 | 16 | 47 | 4348019 | 46.1 | 3.85** | 1.68 | 2.41 |
|  |  |  |  | BPR14197 | 42.9 |  |  |  |
| 11 | 2004 | 16 | 47 | 4348019 | 46.1 | 7.06** | 1.68 | 2.41 |
|  |  |  |  | NKS13-J9 | 40.2 |  |  |  |
| 12 | 2004 | 16 | 46 | 4348019 | 46.0 | 6.87** | 1.68 | 2.41 |
|  |  |  |  | P91M50 | 39.1 |  |  |  |
| 13 | 2004 | 16 | 45 | 4348019 | 46.1 | 4.08** | 1.68 | 2.41 |
|  |  |  |  | MBS53135N | 42.5 |  |  |  |
| 14 | 2004 | 16 | 46 | 4348019 | 46.2 | 6.49** | 1.68 | 2.41 |
|  |  |  |  | P91M40 | 40.2 |  |  |  |
| 15 | 2004 | 16 | 47 | 4348019 | 46.1 | 2.88** | 1.68 | 2.41 |
|  |  |  |  | CSR1514 | 43.6 |  |  |  |
| 16 | 2004 | 16 | 47 | 4348019 | 46.1 | 2.89** | 1.68 | 2.41 |
|  |  |  |  | CSR1500 | 43.5 |  |  |  |
| 17 | 2004 | 16 | 47 | 4348019 | 46.1 | 4.59** | 1.68 | 2.41 |
|  |  |  |  | AG1501 | 42.7. |  |  |  |

TABLE 2-continued

PAIRED COMPARISONS

| Comp # | Year | # of Loc. | # of Obs. | Genotype | Mean Yield | t Value | Critical t @ .05 | Critical t @ .01 |
|---|---|---|---|---|---|---|---|---|
| 18 | 2004 | 16 | 46 | 4348019<br>CSR1512N | 46.2<br>43.1 | 3.26** | 1.68 | 2.41 |

*Significant at .05 level of probability
**Significant at .01 level of probability

DEPOSIT INFORMATION

A deposit of the Stifle Seed Farm, Inc. and Monsanto Technology LLC proprietary soybean cultivar designated 4348019 disclosed above and recited in the appended claims has been made with the American Type Culture Collection (ATCC). 10801 University Boulevard. Manassas. Virginia 20110. The date of deposit was Apr. 4. 2007. The deposit of 2.500 seeds was taken from the same deposit maintained by Stine Seed Farm. Inc. since prior to the filing date of this application. All restrictions upon the deposit have been removed, and the deposit is intended to meet all of the requirements of 37 C.F.R. 1.801-1.809. The ATCC accession number is PTA-8309. The deposit will be maintained in the depository for a period of 30 years. or 5 years after the last reguest. or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention as limited only by the scope of the appended claims.

What is claimed is:

1. A seed of soybean cultivar 4348019, wherein a representative sample of seed of said cultivar was deposited under ATCC Accession No. PTA 8309.

2. A soybean plant, or a part thereof, produced by growing the seed of claim 1.

3. A tissue culture of cells produced from the plant of claim 2, wherein said cells of the tissue culture are produced from a plant part selected from the group consisting of leaves, pollen, embryos, cotyledons, hypocotyls, meristematic cells, roots, root tips, pistils, anthers, flowers, stems and pods.

4. A protoplast produced from the plant of claim 2 or the tissue culture of claim 3.

5. A soybean plant regenerated from the tissue culture of claim 3, wherein the regenerated plant has all the morphological and physiological characteristics of soybean cultivar 4348019.

6. A method for producing an F1 hybrid soybean seed, wherein the method comprises crossing the plant of claim 2 with a different soybean plant and harvesting the resultant F1 hybrid soybean seed.

7. A hybrid soybean seed produced by the method of claim 6.

8. A hybrid soybean plant, or a part thereof, produced by growing said hybrid seed of claim 7.

9. A method of producing an herbicide resistant soybean plant wherein the method comprises transforming the soybean plant of claim 2 with a transgene wherein the transgene confers resistance to an herbicide selected from the group consisting of imidazolinone, sulfonylurea, glyphosate, glufosinate, L-phosphinothricin, triazine and benzonitrile.

10. An herbicide resistant soybean plant produced by the method of claim 9.

11. A method of producing an insect resistant soybean plant wherein the method comprises transforming the soybean plant of claim 2 with a transgene that confers insect resistance.

12. An insect resistant soybean plant produced by the method of claim 11.

13. The soybean plant of claim 12, wherein the transgene encodes a Bacillus thuringiensis endotoxin.

14. A method of producing a disease resistant soybean plant wherein the method comprises transforming the soybean plant of claim 2 with a transgene that confers disease resistance.

15. A disease resistant soybean plant produced by the method of claim 14.

16. A method of producing a soybean plant with modified fatty acid metabolism or modified carbohydrate metabolism wherein the method comprises transforming the soybean plant of claim 2 with a transgene encoding a protein selected from the group consisting of fructosyltransferase, levansucrase, α-amylase, invertase, and starch branching enzyme or encoding an antisense of stearyl-ACP desaturase.

17. A soybean plant having modified fatty acid metabolism or modified carbohydrate metabolism produced by the method of claim 16.

18. A method of introducing a desired trait into soybean cultivar 4348019 wherein the method comprises:

(a) crossing a 4348019 plant, wherein a representative sample of seed was deposited under ATCC Accession No. PTA-8309, with a plant of another soybean cultivar that comprises a desired trait to produce progeny plants wherein the desired trait is selected from the group consisting of male sterility, herbicide resistance, insect resistance, modified fatty acid metabolism, modified carbohydrate metabolism and resistance to bacterial disease, fungal disease or viral disease;

(b) selecting one or more progeny plants that have the desired trait to produce selected progeny plants;

(c) crossing the selected progeny plants with the 4348019 plants to produce backcross progeny plants;

(d) selecting for backcross progeny plants that have the desired trait and the physiological and morphological characteristics of soybean cultivar 4348019 listed in Table 1 to produce selected backcross progeny plants; and (e) repeating steps (c) and (d) three or more times in succession to produce selected fourth or higher backcross progeny plants that comprise the desired trait and all of the physiological and morphological characteristics of soybean cultivar 4348019 listed in Table 1.

19. A plant produced by the method of claim 18, wherein the plant has the desired trait and all of the physiological and morphological characteristics of soybean cultivar 4348019 listed in Table 1.

20. The plant of claim 19, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

21. The plant of claim 19, wherein the desired trait is insect resistance and the insect resistance is conferred by a transgene encoding a *Bacillus thuringiensis* endotoxin.

22. The plant of claim 19, wherein the desired trait is modified fatty acid metabolism or modified carbohydrate metabolism and said desired trait is conferred by a nucleic acid encoding a protein selected from the group consisting of fructosyltransferase, levansucrase, α-amylase, invertase and starch branching enzyme or encoding an antisense of stearyl-ACP desaturase.

* * * * *

UNITED STATES PATENT AND TRADEMARK OFFICE
CERTIFICATE OF CORRECTION

PATENT NO. : 7,291,769 B2 Page 1 of 1
APPLICATION NO. : 11/065321
DATED : November 6, 2007
INVENTOR(S) : William H. Eby It is certified that error appears in the above-identified patent and that said Letters Patent is hereby corrected as shown below:

In column 23, line 15, where "A deposit of the Stifle Seed Farm, Inc." should read, -- A deposit of the Stine Seed Farm, Inc. --

Signed and Sealed this

Eighth Day of April, 2008

JON W. DUDAS
*Director of the United States Patent and Trademark Office*

UNITED STATES PATENT AND TRADEMARK OFFICE
CERTIFICATE OF CORRECTION

PATENT NO.         : 7,291,769 B2
APPLICATION NO.    : 11/065321
DATED              : November 6, 2007
INVENTOR(S)        : William H. Eby It is certified that error appears in the above-identified patent and that said Letters Patent is hereby corrected as shown below:

in column 23, line 15, where "A deposit of the Stifle Seed Farm, Inc." should read, -- A deposit of the Stine Seed Farm, Inc. --

Signed and Sealed this

Twenty Second Day of April, 2008

JON W. DUDAS
*Director of the United States Patent and Trademark Office*